United States Patent
Schoenbach et al.

(10) Patent No.: US 9,872,721 B2
(45) Date of Patent: Jan. 23, 2018

(54) MULTI-ELECTRODE ELECTRICAL PULSE DELIVERY SYSTEM FOR TREATMENT OF BIOLOGICAL TISSUES

(75) Inventors: Karl Schoenbach, Norfolk, VA (US); Richard Heller, Norfolk, VA (US)

(73) Assignee: OLD DOMINION UNIVERSITY RESEARCH FOUNDATION, Norfolk, VA (US)

( * ) Notice: Subject to any disclaimer, the term of this patent is extended or adjusted under 35 U.S.C. 154(b) by 623 days.

(21) Appl. No.: 13/822,010

(22) PCT Filed: Sep. 9, 2011

(86) PCT No.: PCT/US2011/050939
§ 371 (c)(1),
(2), (4) Date: Mar. 11, 2013

(87) PCT Pub. No.: WO2012/033984
PCT Pub. Date: Mar. 15, 2012

(65) Prior Publication Data
US 2013/0172884 A1 Jul. 4, 2013

Related U.S. Application Data

(60) Provisional application No. 61/381,257, filed on Sep. 9, 2010.

(51) Int. Cl.
*A61B 18/12* (2006.01)
*A61B 18/14* (2006.01)
*A61B 18/00* (2006.01)

(52) U.S. Cl.
CPC .......... *A61B 18/14* (2013.01); *A61B 18/1206* (2013.01); *A61B 2018/0016* (2013.01);
(Continued)

(58) Field of Classification Search
CPC .. A61B 2018/0016; A61B 2018/00172; A61B 2018/00178; A61B 2018/00916;
(Continued)

(56) References Cited

U.S. PATENT DOCUMENTS 4,112,950 A * 9/1978 Pike .................... A61B 18/1402
174/115
4,356,466 A * 10/1982 Brown ................... H01H 51/06
335/131
(Continued)

FOREIGN PATENT DOCUMENTS

WO 02068044 9/2002
WO 2006034088 3/2006

OTHER PUBLICATIONS

International Search Report and the Written Opinion of the ISA dated Jan. 6, 2012 in International Application No. PCT/US2011/050939, International filed Sep. 9, 2011. (10 pages).

*Primary Examiner* — Ronald Hupczey, Jr.
(74) *Attorney, Agent, or Firm* — Nixon Peabody LLP; Eduardo J. Quinones

(57) ABSTRACT

Systems and methods for treating or manipulating biological tissues are provided. In the systems and methods, a biological tissue is placed in contact with an array of electrodes. Electrical pulses are then applied between a bias voltage bus and a reference voltage bus of a distributor having switching elements associated with each of the electrodes. The switching elements provide a first contact position for coupling electrodes to bias voltage bus, a second contact position for coupling electrodes to the reference voltage bus, and a third contact position for isolating electrodes from the high and reference voltage buses. The switching elements are operated over various time intervals to provide the first contact position for first electrodes, a second contact position for second electrodes adjacent to the first electrodes, and a third
(Continued)

contact position for a remainder of the electrodes adjacent to the first and second electrodes.

25 Claims, 4 Drawing Sheets

(52) U.S. Cl.
  CPC ... *A61B 2018/124* (2013.01); *A61B 2018/143* (2013.01); *A61B 2018/1467* (2013.01)

(58) Field of Classification Search
  CPC ........... A61B 2018/00922; A61B 2018/00928; A61B 2018/00946; A61B 2018/00952; A61B 2018/1242
  See application file for complete search history.

(56) References Cited

U.S. PATENT DOCUMENTS

| | | | | |
|---|---|---|---|---|
| 5,058,605 A * | 10/1991 | Slovak | ................... | A61N 1/322 607/148 |
| 5,342,356 A * | 8/1994 | Ellman | ................. | A61B 18/14 606/32 |
| 5,443,463 A * | 8/1995 | Stern | ........................ | A61N 1/40 606/51 |
| 5,674,267 A * | 10/1997 | Mir | ........................ | A61N 1/325 604/21 |
| 5,964,726 A * | 10/1999 | Korenstein | ............ | A61N 1/042 435/173.4 |
| 5,993,434 A * | 11/1999 | Dev | ........................ | A61N 1/325 604/20 |
| 6,152,923 A * | 11/2000 | Ryan | ................... | A61B 18/1445 606/42 |
| 6,350,263 B1 * | 2/2002 | Wetzig | ............... | A61B 18/1492 600/374 |
| 6,473,653 B1 * | 10/2002 | Schallhorn | ............... | A61N 1/05 600/393 |
| 7,367,974 B2 * | 5/2008 | Haemmerich | ..... | A61B 18/1477 128/898 |
| 7,520,877 B2 * | 4/2009 | Lee, Jr. | ............... | A61B 18/1206 606/42 |
| 8,100,895 B2 * | 1/2012 | Panos | ................ | A61B 18/1492 606/32 |
| 2007/0088413 A1 * | 4/2007 | Weber | .................... | A61B 18/14 607/99 |
| 2008/0125772 A1 * | 5/2008 | Stone | ................. | A61B 18/1492 606/41 |
| 2008/0221565 A1 | 9/2008 | Eder et al. | | |
| 2010/0022824 A1 | 1/2010 | Cybluski et al. | | |

\* cited by examiner

MULTI-ELECTRODE ELECTRICAL PULSE DELIVERY SYSTEM FOR TREATMENT OF BIOLOGICAL TISSUES

CROSS REFERENCE TO RELATED APPLICATIONS

This §371 National Stage Application claims priority to International Application No. PCT/US11/050939, filed Sep. 9, 2011, which claim priority to U.S. Provisional Patent Application No. 61/381,257, filed Sep. 9, 2010, the entirety of which are incorporated herein by reference.

BACKGROUND OF THE INVENTION

1. Field of the Invention

The present invention is directed to the field of treatment of biological tissues using high voltage pulses, and more specifically to a multi-electrode pulse delivery system for the treatment of biological tissues using high voltage pulses.

2. Background

Cancer is one of the leading causes of disease, being responsible for over half a million deaths in the United States each year. For example, breast cancer is the most common form of malignant disease among women in Western countries and, in the United States, is one of the most common causes of death among women between 40 and 55 years of age. The incidence of breast cancer is increasing, especially in older women, but the cause of this increase is unknown. Malignant melanoma is another form of cancer whose incidence is increasing at a frightening rate, at least sixfold in the United States since 1945, and is the single most deadly of all skin diseases. One of the most devastating aspects of cancer is the propensity of cells from malignant neoplasms to disseminate from their primary site to distant organs and develop into metastases. Despite advances in surgical treatment of primary neoplasms and aggressive therapies, many cancer patients die as a result of metastatic disease.

To treat such cancers, several cancer therapies have been developed that are based on the application of electric fields to a tumor containing malignant cancerous cells. Some of these therapies involve the use of radiofrequency or microwave devices to cause heating of the tumor to kill cancerous cells via hyperthermia. Other therapies use electrical pulses to permeabilize the cancerous cells in the tumor to allow the introduction of toxic drugs. In yet other therapies, short, high voltage electrical pulses can be used as a purely standalone cancer therapy that kills tumors and abnormal cells without hyperthermia or drugs.

Unfortunately, a typical tumor generally extends over an area that exceeds the area that can be efficiently and/or effectively treated covered using conventional electrical pulse treatment systems. Conventional systems typically rely on electrode devices that are either needles, which are inserted into the tissue, or pins, which are placed on top of the tissue. Needles generally allow electric fields to be formed at any depth, limited primarily by the length of the needles. In contrast, pins allow the electric field to penetrate only a limited depth of the tissues, determined by the extent of the fringe electric field.

In many conventional electrical pulse systems, a pair of electrodes is typically used to generate electric fields using voltage pulses. In operation, the electrodes are manually placed on or near the tissue to be treated. Thereafter, a voltage pulse is applied across the electrodes to form an electric field for providing treatment. However, a two electrode arrangement can effectively only cover an area or volume having a generally elliptical shape with boundaries for electroporation or nanoporation determined by the electrode distance (generally limited to between 0.5 cm and 1.0 cm) and the applied voltage. Although a larger gap or spacing can be provided, such an arrangement can require application of a higher voltage pulse to generate the necessary electric field and/or providing longer pulse durations at the electrodes to ensure that a therapeutic electric field intensity is provided to all tissues to be treated. Further, such a configuration will require higher voltage generators and additional cabling requirements, which can lead to an overall higher cost.

To provide for treatment of a larger area or volume, some conventional systems use a larger number of electrodes. In a typical configuration, one electrode is provided that is surrounded by other electrodes. An electric field is then generated by applying a voltage pulse between the center electrode and the surrounding electrodes. Although such an arrangement allows a larger area or volume to be treated, such a configuration has several drawbacks. First, to expand the treatment area, a power supply providing a higher current (i.e., a larger power) would be needed. Second, even when such power supplies are available, the area or volume that can be treated can also be limited by the maximum voltage per distance between electrodes. An alternative is to use multiple power supplies with the multiple electrodes. However, the use of multiple power supplies requires a greater amount of power and complexity for managing the multiple power supplies.

SUMMARY

The invention concerns systems and methods for the treatment of biological tissues using high voltage pulses. In a first embodiment of the invention, a device for treatment of biological tissues is provided. The device includes a plurality of electrodes, a bias voltage bus, a reference voltage bus, one or more switching elements associated with each of the plurality of electrodes, and a control system for controlling the switching elements. In the device, the switching elements associated with each of the plurality of electrodes are configured to provide a first contact position for electrically coupling an associated one of the electrodes to the bias voltage bus, a second contact position for electrically coupling the associated one of the plurality of electrodes to the reference voltage bus, and a third contact position for electrically disconnecting the associated one of the plurality of electrodes from the reference voltage and bias voltage buses. Further, the control system is configured for independently selecting one of the first, second, and third contact positions for the switching element during a plurality of time intervals, where during each of the plurality of time intervals, the control system is configured for selecting the first contact position for a first one of the plurality of electrodes, a second contact position for a second of the plurality of electrodes adjacent to the first of the plurality of electrodes, and a third contact position for at least a remainder of the plurality of electrodes adjacent to the first and second of the plurality of electrodes.

The device can further include a voltage source configured for applying a voltage pulse between the bias voltage bus and the reference voltage bus. The applied voltage pulse can have a voltage from 0.01 kV to 100 kV, the duration of the voltage pulses can be between 700 picoseconds and 2 seconds, and the frequency of the voltage pulses can be between 1 Hz and 1 MHz. In the device, The control system can configured to alternate between the first, second, and third contact positions to cause the plurality of electrodes to provide voltage pulses.

The device can have an electrode-to-electrode spacing for the plurality of electrodes that is between 0.5 mm and 10 mm.

In the device, the switching element can include a first actuator operable to electrically connect the associated one of the plurality of electrodes to the bias voltage bus in response to a first signal from the control system for selecting the first contact position, and a second actuator operable to electrically connect the associated one of the plurality of electrodes to the reference voltage bus in response to a second signal from the control system for selecting the second contact position.

In a second embodiment of the invention, a device for the treatment of biological tissues is provided. The device can include a power supply for generating electrical pulses, an array of electrodes, a distributor comprising one or more switching elements associated with each of the electrodes, and a controller for controlling the switching elements. In the device, switching elements are configured to provide a first contact position for electrically coupling an associated one of the electrodes to a high voltage terminal of the power supply, a second contact position for electrically coupling the associated one of the electrodes to a reference voltage terminal of the power supply, and a third contact position for electrically isolating the associated one of the electrodes from the power supply.

In the device, during each of the plurality of time intervals, the control system is configured for selecting the first contact position for a first one of the electrodes, a second contact position for a second of the electrodes adjacent to the first of the electrodes, and a third contact position for at least a remainder of the electrodes adjacent to the first and second of the electrodes.

The device can also include a substrate portion mechanically coupled to an endpiece portion of the distributor, where the substrate portion is configured for supporting the plurality of electrodes. The substrate can be removably coupled to the endpiece portion.

In the device, the power supply is configured for generating voltage pulses having a voltage from 0.01 kV to 100 kV, a duration from 700 picoseconds to 2 seconds, and a frequency between 1 Hz and 1 MHz.

In the device, the switching elements associated with each of the plurality of electrodes include a first switch device to electrically connect the associated one of the electrodes to the high voltage terminal in response to a first signal from a control system for selecting the first contact position, and a second switch operable to electrically connect the associated one of the electrodes to the reference voltage terminal in response to a second signal from the control system for selecting the second contact position.

In the device, the distributor further includes a first electrically conductive plate electrically coupled to the high voltage terminal, a second electrically conductive plate coupled to the reference voltage terminal, and a plurality of contacts disposed between the first and second plates and electrically isolated from the first and second plates, where each of the plurality of contacts is electrically coupled to one of the electrodes.

In the device, the switching elements associated with each one of the electrodes include a first actuator for simultaneously contacting the first plate and a one of the plurality of contacts associated with the one of the electrode in response to a signal from controller to provide the first contact state, and a second actuator for simultaneously contacting the second plate and a one of the plurality of contacts associated with the one of the electrode in response to a signal from controller to provide the second contact state. The first and second actuators can include linear actuators.

In the device, the plurality of contacts and the switching elements can be arranged in a substantially circular path. Further, an electrode-to-electrode spacing for the array of electrodes is between 0.5 mm and 10 mm. Additionally, the array of electrode can include a plurality of penetrating needles or a plurality of non-penetrating pins.

In a third embodiment of the invention, a method for treating or manipulating biological tissues is provided. The method includes placing a biological tissue in contact with an array of electrodes. The method also includes applying one or more electrical pulses between a bias voltage bus and a reference voltage bus of a distributor comprising one or more switching elements associated with each of the electrodes and operable to provide a first contact position for electrically coupling an associated one of the electrodes to bias voltage bus, a second contact position for electrically coupling the associated one of the electrodes to the reference voltage bus, and a third contact position for electrically isolating the associated one of the electrodes from the high voltage and reference voltage buses. The method further includes operating the switching elements over a plurality of time intervals, In the method, during each of the plurality of time intervals, the switching elements are operated to provide the first contact position for a first one of the electrodes, a second contact position for a second of the electrodes adjacent to the first of the electrodes, and a third contact position for at least a remainder of the electrodes adjacent to the first and second of the electrodes.

In the method, the step of applying further includes selecting the electrical pulses to provide voltage difference from 0.01 kV to 100 kV, selecting the electrical pulses to have a duration between 700 picoseconds and 2 seconds, and selecting the electrical pulses to have a frequency of the voltage pulses is between 1 Hz and 1 MHz.

In the method, the step of placing further includes selecting an array of electrodes comprising at least a 2×2 array of electrodes and the step of operating can further includes selecting as the first one and the second one of the electrodes a first diagonal pair of the 2×2 array during a first of the plurality time intervals, and selecting as the first one and the second one of the electrodes a second diagonal pair of the 2×2 array during a second of the plurality time intervals.

In the method, the step of operating can further includes determining a location of the biological tissue relative to positions of electrodes in the array, identifying a portion of the electrodes in the array capable of producing an electric field capable of inducing a cell effect in the biological tissue, and selecting the first one and the second one of the electrodes from the identified portion of the electrodes.

DETAILED DESCRIPTION

Figure 1:
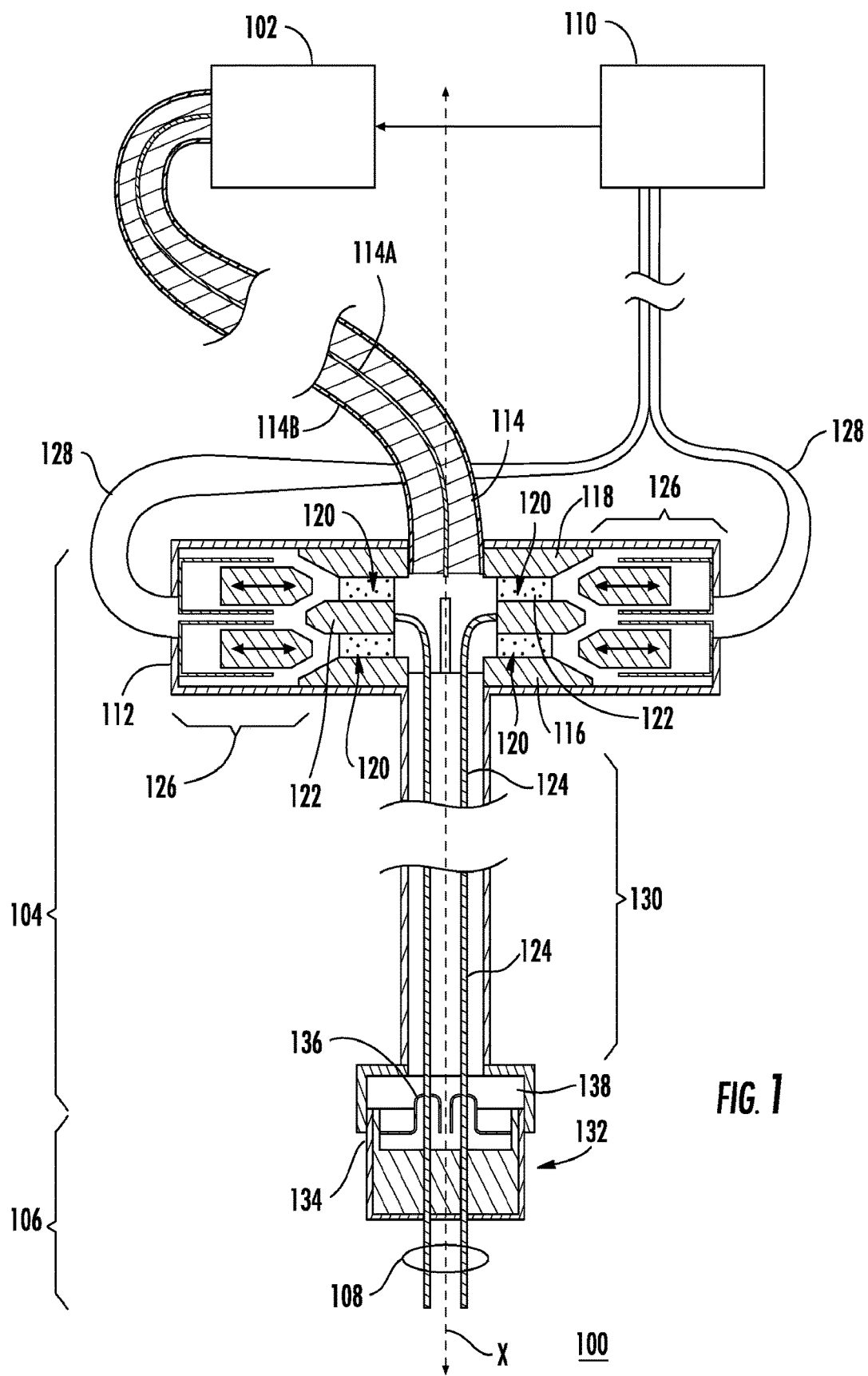
FIG. 1 is a partial cross-section side view of an exemplary delivery system configured in accordance with an embodiment of the invention.

The invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The invention is not limited by the illustrated ordering of acts or events, as some acts may occur in different orders and/or concurrently with other acts or events. Furthermore, not all illustrated acts or events are required to implement a methodology in accordance with the invention.

Several definitions that apply throughout this document will now be presented. The term "biological tissue" refers to any type of live or dead cells from an organism, including cells that are located on or in the organism or tissues that have been excised or otherwise removed from the organism. The term "cell function" refers to any biological activity, process, behavior or result that a cell is capable of performing, exhibiting or undergoing. The term "cell death" refers to the biological death of a cell. The term "treatment" refers to an alteration of the cell function of a cell, including causing cell death, or the inducement of changes in the structure, membrane, location, or physical characteristics of cells in the biological tissue.

As described above, the main limitation of using of electric pulses for the treatment of biological tissues is that the area or volume which can be treated using a conventional set of electrodes is typically limited unless multiples electrodes and multiple power supplies are provided. However, as described above, such alternate configurations are generally not advantageous with respect to providing efficient and effective treatment. Further, conventional configurations typically do not provide flexibility in providing treatment. For example, such configurations do not generally permit the directionality of the electric fields generated to be altered without a significant reconfiguration of the electrodes and the power supplies. Additionally, such configurations are generally limited with respect to the targeting of specific biological tissues during treatment.

In view of these limitations, the various embodiments of the invention provide a new programmable, multi-electrode electrical pulse delivery system for treatment of biological tissues of any size. In particular, a delivery system in accordance with the various embodiments of the invention includes an array of electrodes to be placed on or near the biological tissues to be treated, a power supply to generate electrical pulses, and a distribution system for selectively connecting the array of electrodes to the power supply. In operation, the distributor system is configured for sequentially connecting different pairs of electrodes to the power supply to generate a series of electric fields for treatment of biological tissues. An exemplary configuration for such a delivery system is illustrated with respect to FIGS. 1, 2, and 3.

FIG. 1 is a partial cross-section side view of an exemplary delivery system 100 configured in accordance with an embodiment of the invention. As shown in FIG. 1, system 100 includes a power supply 102, a distributor 104, an endpiece portion 106 including electrodes 108, and a controller 110. Together, controller 110 and distributor 104 form a distribution system for selectively coupling electrodes 108 to power supply 102.

In the exemplary configuration of FIG. 1, the power supply 102 can be any high voltage power supply capable of generating electrical pulses suitable for therapeutic use. For example, power supply 102 can be configured to provide voltage pulses with amplitudes that can range from 0.01 kV to 100 kV. Further, the power supply 102 can also be configured to provide a duration of such pulses that varies from 1 nanosecond to 2 seconds. The pulses can be monopolar, bipolar, or oscillating. Additionally, a frequency of the pulses can range from 1 Hz to 1 MHz. However, the various embodiments of the invention are not limited in this regard and the power supply can be configured for delivery of pulses of any other amplitude, duration, or otherwise meeting any other criteria. In some embodiments, the amplitude, duration, and other characteristics of the pulses can be controlled by signals from controller 110 or another control device. In other embodiments, controls can be provided at power supply 102 for selecting amplitude, duration, and any other characteristics of the pulses.

The actual configuration of a power supply in the various embodiments of the invention can vary according to the type of treatment to be performed. That is, a power supply in accordance with the various embodiments of the invention can be configured to provide electrical pulses or a continuous electrical signal.

Distributor 104 can be electrically coupled to power supply 102 via one or more cables 114. For example, as shown in FIG. 1, cable 114 can be a coaxial cable with an inner conductor 114A and an outer conductor 114B coupled to the high voltage terminal and low or reference (ground) voltage terminal, respectively, of power supply 102. However, the various embodiments are not limited in this regard and other types of cables and/or connections can be used to couple power supply 102 to distributor 104.

In the various embodiments of the invention, the distributor 104 can include a support portion 112 for supporting and/or housing the various components of distributor 104. In particular, support portion 112 is configured to support components for selectively connecting or disconnecting each of the electrodes 108 from one of the terminals of power supply 102. These components include a bias voltage bus 116 coupled to a high voltage terminal of power supply 102 and a reference voltage bus 118 coupled to a low or reference voltage terminal of the power supply 102. In distributor 104, the buses 116 and 118 are electrically isolated from each other.

In the various embodiments, each of buses 116 and 118 can be formed in several ways. For example, as shown in FIG. 1, the buses 116 and 118 can be electrically conductive portions arranged in a stacked configuration, where the buses 116 and 118 are separated by one or more electrically insulating dielectric portions 120. In such an arrangement, inner conductor 114A is coupled to bus 116 and outer conductor 114B is coupled to bus 118. However, the various embodiments of the invention are not limited to the exemplary configuration of FIG. 3 and any other arrangements for buses 116 and 118 and/or for coupling buses 116 and 118 to power supply 102 can be used without limitation.

The components of distributor 104 further include contacts 122 that are electrically coupled to the electrodes 108 via cables 124. The contacts 122 and cables 124 are disposed and/or insulated in support 112 such that they are also electrically isolated from buses 116 and 118.

In the various embodiments of the invention, the buses 116 and 118, the contacts 122, and the cables 124 can be arranged in a variety of ways. For example, as shown in FIG. 1, the components are arranged in a stack consisting of the bus 116, contacts 122, and bus 118, where each of these components is kept electrically and physically isolated via one or more dielectric portions 120 therebetween. In one exemplary configuration, the contacts 122 and buses 116 and 118 can be arranged in a circular pattern, as shown in FIG. 2.

Figure 2:
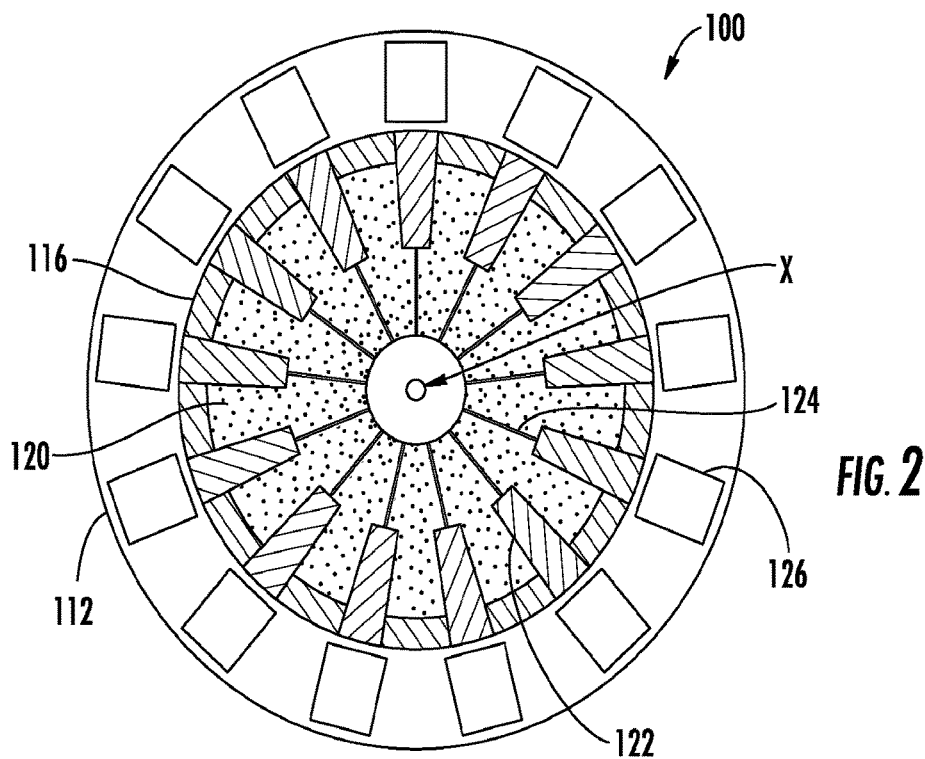
FIG. 2 is a cross-section top down view of the exemplary delivery system in FIG. 1.

FIG. 2 is a cross-section top down view of exemplary delivery system 100. In particular, FIG. 2 is a cross-section view just above contacts 122. As shown in FIG. 2, the contacts 122 are placed in a circular pattern about a central axis (X) of support 112 on or in dielectric portions 120 and over bus 116. In such a configuration, the buses 116 and 118 can be configured as circular, annular, or disc-like plates, as shown in FIG. 2, with an outer diameter substantially corresponding to the outer diameter defined by the contacts 122. As further shown in FIG. 2, each of contacts 122 is electrically coupled to one of cables 124 (and thus to one of electrodes 108 in FIG. 1). Further, as shown in FIGS. 1 and 2, the cables 124 extend from contacts 122 and down along the central axis (X) of support 112 to endpiece 106.

However, the various embodiments of the invention are not limited to circular and/or radial arrangements of the buses 116 and 118 and the contacts 122. Rather, any linear or non-linear arrangement of contacts 122 and buses 116 and 118 can be used in the various embodiments.

As described above and referring back to FIG. 1, the electrodes 108 are selectively coupled to one of the terminals of power supply 102. In particular, the distributor 104 provides such capability via the use of one or more switching elements 126 associated with each of the contacts 122 (and thus with each of the electrodes 108) that are controlled by controller 110. In particular, the switching elements 126 are configured in distributor 104 to provide at least three contact positions for each of contacts 122 (and thus each of electrodes 108). These contact positions can be selected independently for each of the connectors via control signal provide via signal lines 128 coupled to controller 110.

In a first contact position, the switching elements 126 associated with a one of the contacts 122 are configured to electrically connect the associated one of the contacts 122 to the bias voltage bus 116. In a second contact position, the switching elements 126 are configured to electrically connect the associated one of the contacts 122 to the reference voltage bus 118. In a third contact position, the switching elements 126 are configured to electrically disconnect the associated one of the contacts 122 from both buses 116 and 118. Thus, each of contacts 122 (and thus each of electrodes 108) can be individually connected to one of the high and low voltage terminals of power supply 102 or left floating.

In one embodiment of the invention, the switching elements 126 can be implemented using a series of linear actuators with electrically conductive plungers. In such configurations, the actuators can be disposed in support 112 such that when an actuator is activated, the plunger physically and electrically connects one of the contacts 122 to one of the buses 116 and 118. In the configuration illustrated in FIG. 1, two actuators are provided for each of contacts 122, as described in greater detail below with respect to FIGS. 3A, 3B, and 3C.

In the various embodiments, any types of actuator devices can be used, including linear and non-linear actuator devices. These devices can be powered and/or controlled via various methods. For example, actuator devices can be mechanical, hydraulic, pneumatic, piezoelectric, or electromechanical, to name a few. However, any other type of actuator device can also be used without limitation.

Figure 3B:
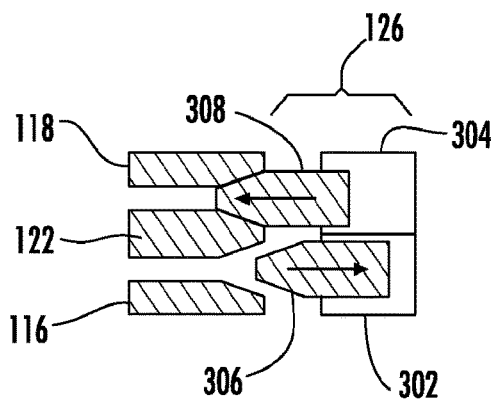
FIGS. 3A, 3B, and 3C are diagrams illustrating the operation of the switching elements in FIG. 1, when implemented using linear actuators, for an associated one of the contactors for the first, second, and third contact positions, respectively.
Figure 3A:
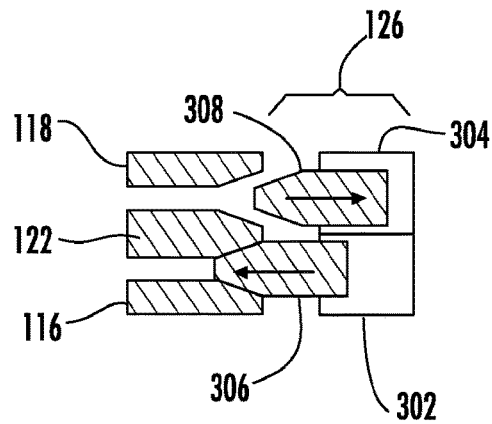
Figure 3C:
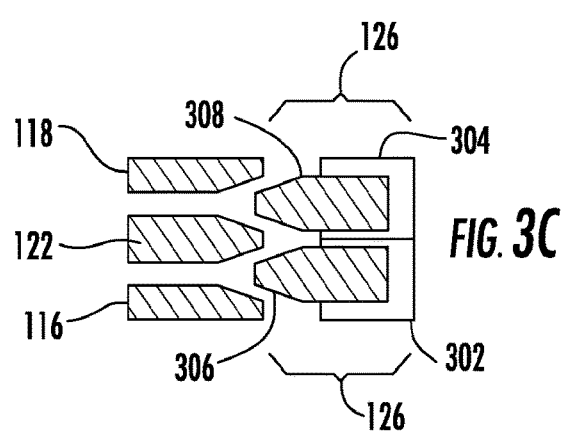

FIGS. 3A-3C are diagrams illustrating the operation of the switching elements 126, when implemented using linear actuators, for an associated one of the contactors 122 for the first, second, and third contact positions. In FIGS. 3A-3C, the switching elements 126 are configured as a first actuator 302 and a second actuator 304, providing a first plunger 306 and a second plunger 308, respectively. The first actuator 302 is configured so that when first plunger 306 is extended, a physical and electrical connection is provided between a one of contacts 122 and bias voltage bus 116. Similarly, the second actuator 304 is configured so that when second plunger 308 is extended, a physical and electrical connect is provided between a one of contacts 122 and reference voltage bus 118.

The first contact position for a one of contacts 122 is illustrated in FIG. 3A. For the first contact position, the controller 110 generates signals for operating actuator 302 to cause plunger 306 to extend. Thus, the one of contacts 122 (and also an associated one of electrodes 108) is electrically coupled to bus 116 via plunger 306. In the first contact position, signals can also be provided for operating actuator 304 to cause plunger 308 to retract. Thus, the one of contacts 122 is not in electrical contact with bus 118 in order to avoid shorting bus 116 to bus 118 via the one of contacts 122. The present disclosure contemplates that for some types of actuator devices, a plunger will revert to a retracted state when a signal to operate the actuator device is not provided. Accordingly, in some configurations, no signal is provided for actuator 304 when a first contact position is needed, resulting in retraction of plunger 308.

The second contact position is illustrated in FIG. 3B. For the second contact position, the controller 110 generates signals for operating actuator 304 to cause plunger 308 to extend. Thus, the one of contacts 122 (and also an associated one of electrodes 108) is electrically coupled to bus 118. Signals can also be provided for operating actuator 302 to cause plunger 306 to retract. Thus the one of contacts 122 will not be in electrical contact with bus 116 in order to avoid shorting bus 118 to bus 116 via the one of contacts 122. As described above, a plunger in some types of actuator devices will revert to a retracted state when a signal to operate the actuator device is not provided. Accordingly, in some configurations, no signal is provided for actuator 302 when the second contact position is needed, resulting in retraction of plunger 306.

The third contact position is illustrated in FIG. 3C. For the third contact position, signals can be provided for operating actuators 302 and 304 to cause plungers 306 and 308 to retract. Thus, the one of contacts 122 will not be in electrical contact with bus 116 or bus 118. In this configuration, the electrode associated with the one of contacts 122 stays on floating potential. However, as described above, a plunger in some types of actuator devices will revert to a retracted state when a signal to operate the actuator device is not provided. Accordingly, in some configurations, no signal is provided for actuators 302 and 304 when the third contact position is needed, resulting in retraction of plungers 306 and 308.

In some embodiments of the invention, the shape of the surfaces of buses 116 and 118, contacts 122, and plungers 306 and 308 can be selected to promote an improved electrical contact. In particular, as shown in FIGS. 3A-3C, slanted corresponding surfaces can be provided. Thus when one of plungers 306 and 308 is extended, the corresponding surfaces of contacts 122 and buses 116 and 118 come into contact with the extending plungers. As a result, a large surface for electrical contact is provided, resulting in a good electrical contact. Further, such a configuration allows compensation for misalignment of the plungers 306 and 308 with respect to components 116, 118, and 122. Although one exemplary configuration for the surface shapes is illustrated in FIGS. 3A-3C, the various embodiments of the invention are not limited in this regard, and other shape configurations can be used in the various embodiments of the invention without limitation.

Although the distributor 104 has described above with respect to the use of actuators for forming the switching elements 126, the various embodiments are not limited in this regard. Rather, in other embodiments, any other type of switch devices can be used to implement switching elements 126. For example, contactors, relays, electronic switches, piezoelectric switches, or any other type of electromechanical or solid state switches can be used in the various embodiments of the invention.

Further, although communication between controller 110, power supply 102, and distributor 104 has been described generally with respect to wireline communications links, the various embodiments are not limited in this regard. In some embodiments of the invention, the communications links used by controller 110 can include one or more wireless communications segments.

Referring back to FIG. 1 and as described above, device 100 also includes an endpiece 106 including a plurality of electrodes 108. Although FIG. 1 shows that endpiece 106 includes only two electrodes, this is for ease of illustration only. Rather, in the various embodiments of the invention, the plurality electrodes 108 can include more than two electrodes. In the various embodiments of the invention, each of the electrode 108 can be penetrating needles, which are inserted into the tissue, or non-penetrating pins, which are placed on top of the tissue. Penetrating needles generally allow electric fields to be formed at any depth, limited primarily by the length of the needles. In contrast, non-penetrating pins allow the electric field to penetrate only a limited depth of the tissues, determined by the extent of the fringe electric field.

In at least some embodiments, the plurality of electrodes 108 are arranged in an array and are electrically coupled to cables 124 in support 112. The cables 124 can be bundled together to minimize the inductance of the entire cable system and therefore reduce distortions in the electric pulses being delivered to the electrodes 108. Further, the cables 124 can travel through a grounded guide portion 130 of support 112 to reduce inductances further. For example, portion 130 can be coupled to bus 118 or other otherwise held at a ground voltage.

In one configuration, the endpiece 106 comprises a substrate 132 for supporting the electrodes 108. In the various embodiments, the substrate 132 can range from substantially rigid substrates to flexible substrates. In the case of a rigid substrate, the substrate can have a fixed, pre-defined shape that can be applied to a particular portion of the patient's skin. In some cases, such substrates can be customized for the particular patient. However, the various embodiments of the invention are not limited in this regard and the substrate can be configured to allow at least one portion of the substrate 132 to be deformable. Accordingly, the semi-rigid substrate can be shaped prior to treatment. Further such a substrate could be reused for the same or other patients. In the various embodiments of the invention, substantially electrically insulating or electrically semi-insulating materials can be used to for the substrates. However, the precise composition for the substrates can vary according to the amount of flexibility required. For example, in the case of rigid substrate, substantially non-deformable materials can be used, such as thick or stiff polymers, ceramics, glass, porcelain, semiconductors, and any combinations thereof, to name a few. In contrast, in the case of flexible materials, substantially deformable materials can be used, such as flexible or deformable polymer, cloth, or paper-like materials. In some cases, flexible or deformable substrates can be provided using a combination of non-deformable materials with deformable or flexible joint structures or joint materials.

As shown in FIG. 1, the substrate 132 can be configured to have the electrodes 108 extend from a first surface of the substrate 132 and to have one or more connector structures 134 for mating with plug-ins 136 at a connecting end 138 of support 112. The plug-ins 136 thus connect the electrodes 108 to cables 124. In some configurations, the substrate 132 and connecting end 138 can be integrally formed. In other configurations, the substrate 132 can be removably attached to connecting end 138. For example, one or more fasteners can be provided endpiece 106 and/or substrate 132. Alternatively, the connector structures 134 and plug-ins 136 can be configured to provide mated parts that are also configured to retain substrate 132 on connecting end 138. Such configurations are advantageous for purposes of providing a disposable substrate 132 or to allow different configurations of substrate 132 (i.e., different electrode configurations) to be used with distributor 104. Further, to facilitate use and reduce the risk of erroneous treatment regimes, the connector structures 134 and plug-ins 136 can be configured to allow their connection in a single orientation.

In some embodiments, the substrate 132 and/or endpiece 106 can also include additional features to facilitate positioning and attachment of the electrodes 108 to a patient. For example, substrate can include an adhesive layer to maintain a substrate in contact with the patient. Such a configuration is particularly useful in the case of a pin-type configuration for the electrodes. Further, the substrate 132 can wetted with an insulating liquid, such as oil, to reduce the probability for electrical breakdown across the surface of the tissue. In another example, the endpiece fasteners for attaching the endpiece to the patient and fixing the position of the endpiece 106 and substrate 132 fixed with respect to the patient. Such methods are well-known in the art and will not be described here.

Although the device illustrated in FIG. 1 relies on a substrate to support and place the electrodes with respect to the biological tissues, the present disclosure contemplates that the distributor 104 can be utilized with manually placed electrodes. In such configurations, after the electrodes are placed, a map of the electrodes can be made to guide operation of distributor. For example, the controller 110 can be provided a map of the electrodes. In another configuration, optical recognition techniques can be used to determine the map of the electrodes.

The device illustrated in FIG. 1 and similar devices in accordance with the various embodiments of the invention thus permit an array of electrodes to be used over a relatively large area. This configuration is advantageous in that a large of array of electrodes can be powered without the need for multiple power supplies. Further, the array of electrodes can be spaced such that therapeutic electric fields can be provided without the need for generating a relatively high electric field or providing excessively long pulses, as in some conventional multiple electrode configurations. Use of device 100 and similar devices will now be described with respect to FIGS. 4, 5, and 6.

Figure 4:
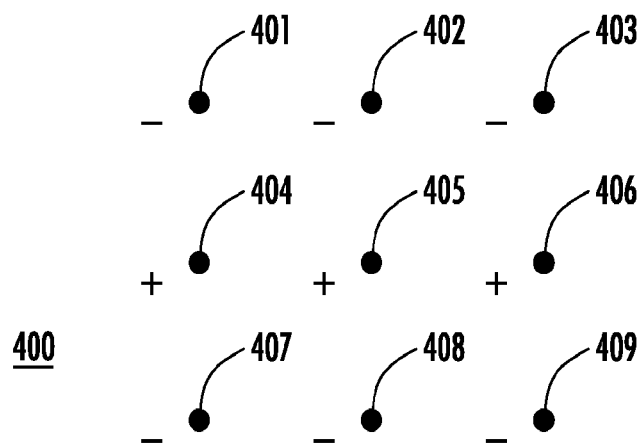
FIG. 4 is a schematic of an exemplary electric field configuration for an array of electrodes in a delivery system configured in accordance with the various embodiments of the invention.

FIG. 4 is a schematic of an exemplary electric field configuration 400 for an array of electrodes 401-409 in a delivery system configured in accordance with the various embodiments of the invention. In the various embodiments of the invention, the electrodes 401-409 are configured as described above. That is, the electrodes 401-409 are positioned in array such that when a voltage pulse is applied by a selected power supply between any two neighboring electrodes in array 100, the resulting electric field will be therapeutic (i.e., provide a desirable or intended treatment for the cells in the biological tissue). In FIG. 4, electrodes 401-409 are distributed in a 3×3 array of electrodes. For a power supply providing electrical pulses with voltages ranging from 10 V to 100 kV, an electrode-to-electrode spacing of less than 1 cm, such as between 0.5 mm and 10 mm, can be provided. For example, in some embodiments of the invention, the electrodes can be spaced between 1 to 8 mm apart. In the case of a 3×3 array of electrodes, this would provide an exposed area between 2 mm×2 mm (for 1 mm spacing) and 1.6 cm×1.6 cm (for 8 mm spacing)

The electric field configuration 400 is one in which alternating rows of electrodes are oppositely polarized. That is, electrodes 401-403 and electrodes 407-409 are biased to a low or reference voltage and electrodes 404-406 are biased to a high voltage when voltage pulses are applied. In some conventional systems, such a configuration would be provided by coupling electrodes 404-406 to a high voltage terminal of a power supply and simultaneously coupling electrodes 401-403 and electrodes 407-409 to a low or reference voltage terminal. However, such a configuration would typically require a significant amount of current and consequently power to deliver the necessary electric field. In other conventional systems, such a configuration would be provided by coupling each of electrodes 404-406 to different power supplies.

In contrast, the various embodiments of the invention provide voltage pulses to each pair of electrodes sequentially. That is, at any one time, only a neighboring or adjacent pair of electrodes is coupled to the power supply, while the remaining electrodes are left floating. For example, the electrodes can be powered in the following sequence (404, 401), (405, 402), (406, 403), (406, 409), (405, 408), (404, 407) to treat the same area as the conventional methods described above. The notation (x, y) shown above refers to the pair of electrodes receiving a pulse (pulsed pair) at a point in the sequence, wherein x refers to the electrode being coupled to the high voltage terminal of the power supply and y refers to the electrode being coupled to the low or reference voltage terminal of the power supply. As a result of configuring the electrodes according to sequence above instead of simultaneously, an electric field is induced in only one portion of the biological tissues at any one time by the electrodes receiving the pulse. The remaining electrodes stay on a floating potential, i.e., an electrical potential which is determined by the electric field distribution caused by the electrodes receiving the pulse.

An additional advantage of the present invention is that the addressable and reconfigurable nature of the delivery system results in the electrodes 401-409 being able to provide electric fields in different directions. In general, the effectiveness of the high energy pulse treatments depends not only on the amplitude and duration of the electric field which is generated by the applied voltage, but also by its direction. Accordingly, it is generally desirable to have the capability to change the direction of the electric fields being induced by the electrodes. The various embodiments of the invention allow such changes in direction by applying power sequentially to electrode pairs in an order and an orientation such that the resulting electric field direction are changed during the treatment. This is conceptually illustrated with respect to FIG. 5.

Figure 5:
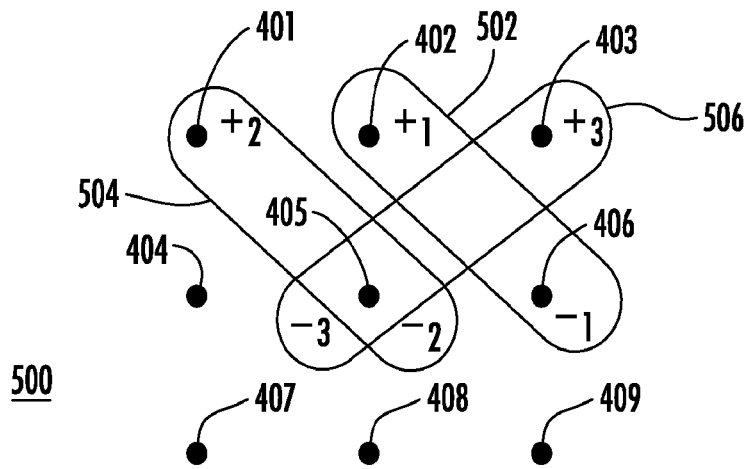
FIG. 5 is a schematic of another exemplary electric field configuration for an array of electrodes in a delivery system configured in accordance with the various embodiments of the invention.

FIG. 5 is a schematic of another exemplary electric field configuration 500 for the array of electrodes 401-409 in a delivery system configured in accordance with the various embodiments of the invention. As shown in FIG. 5, voltage pulses can be applied to the electrodes to produce electric fields. For example, the sequence (402, 406), (401, 405), and (403, 405) can be provided. As a result of this sequence, electric fields oriented in a first direction are provided by pulsed diagonal pairs (402, 406) and (401, 405) in regions 502 and 504 respectively. Thereafter, an electric field oriented in a second direction is provided by pulsed diagonal pairs (403, 405). Such a sequence not only generates electric fields in different directions, but more importance provides different electric field directions for specific area. In particular, a 90 degree change in the electric field direction is provided in the intersection of region 506 and either of regions 502 and 504.

An additional advantage of the various embodiments of the invention is the ability to provide electric fields to treat biological tissues with irregular geometries. That is, in most cases the biological tissue which is to be treated does not necessarily have a shape which fits to an existing electrode array. However, since the electrodes in the various embodiments of the invention can be individually activated, only the electrodes which cover the relevant tissue can be activated. This is illustrated below with respect to FIG. 6.

Figure 6:
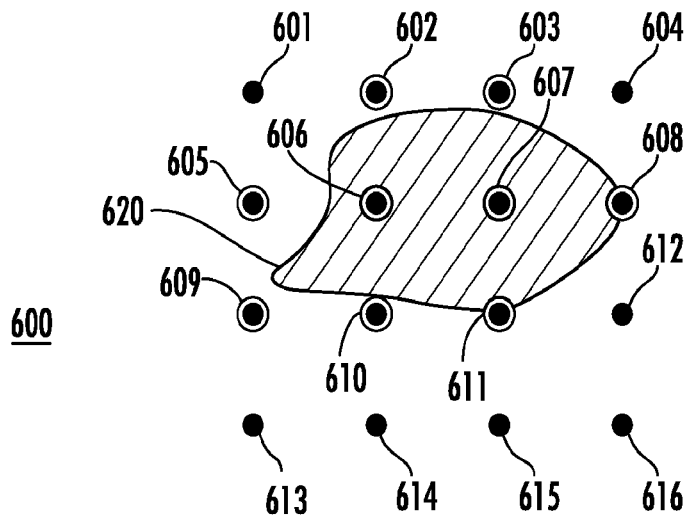
FIG. 6 is a schematic of another exemplary electric field configuration for an array of electrodes in a delivery system configured in accordance with the various embodiments of the invention and disposed over a biological tissue of interest.

FIG. 6 is a schematic of another exemplary electric field configuration 600 for an array of electrodes 601-616 in a delivery system configured in accordance with the various embodiments of the invention and disposed over a biological tissue 620 of interest. In general, it is desirable to limit exposure of high electric field pulses to only the portion of the biological tissues needing treatment. This is primarily for the reason that it is undesirable to induce cell effects in healthy tissues. Accordingly, because the order and orientation of the pulsed pairs is selectable in the various embodiments of the invention, treatment can be limited only to the biological tissue of interest.

For example, as shown in FIG. 6, the array of electrodes 601-616 substantially overlaps the area associated with biological tissue 620 to be treated. In view of the position of biological tissue 620 with respect to electrodes 601-616, only electrodes 602, 603, and 605-611 are needed since only these electrodes generate electric field that would affect a portion of biological tissue 620. The remaining electrodes can be configured to float at all times as described above.

In the exemplary configuration described above, the pulsed pairs and their order can be selected manually or automatically. In the case of automatic selection, a controller, such as controller 110 in FIG. 1, can be configured to identify the position of the electrodes relative to biological tissues of interest and determine the necessary pulsed pairs and order based on various types of information. For example, the pulsed pairs and their order can be selected on information such as: the type of biological tissue being treated, the types of electrodes being used, and capabilities of the power supply, to name a few. However, the various embodiments of the invention are not limited in this regard and other criteria can be used to determine an appropriate sequence for treatment.

The invention also includes the method of treating biological tissues using the above principles. This method involves placing the electrodes at or near the biological tissues of interest and thereafter applying electric field sequentially using sequence pairs, similar to the methods described above.

Figure 7:
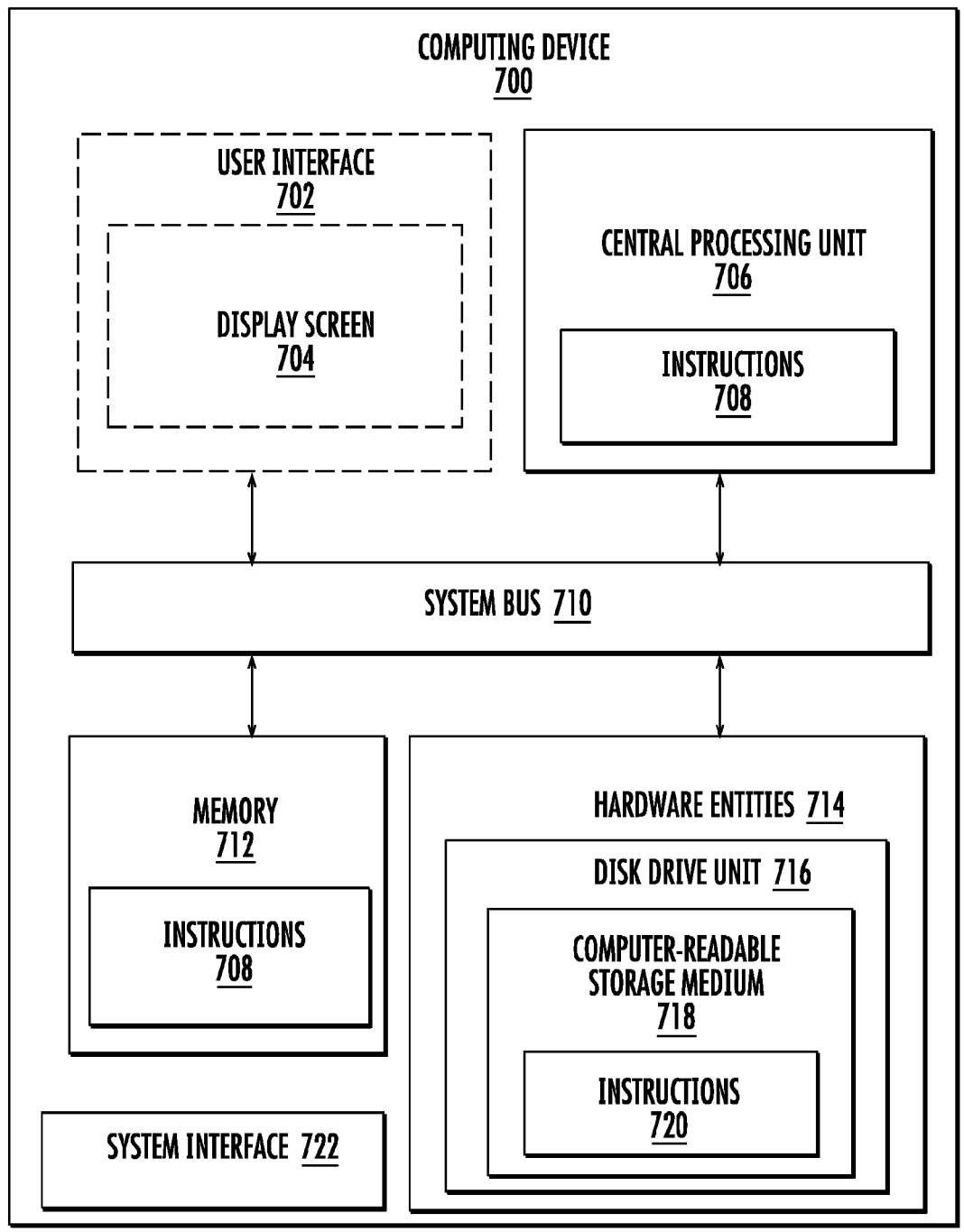
FIG. 7 is block diagram of a computing device which can be implemented as control system in accordance with an embodiment of the invention.

Referring now to FIG. 7, there is provided a detailed block diagram of an exemplary computing device 700 which can be implemented as controller 110 in FIG. 1. Although various components are shown in FIG. 7, the computing device 700 may include more or less components than those shown in FIG. 7 and in a different arrangement as shown in FIG. 7. However, the components shown are sufficient to disclose an illustrative embodiment of the invention. The hardware architecture of FIG. 7 represents only one embodiment of a representative computing device for controlling a jointed mechanical device.

As shown in FIG. 7, computing device 700 includes a system interface 722, a Central Processing Unit (CPU) 706, a system bus 710, a memory 712 connected to and accessible by other portions of computing device 700 through system bus 710, and hardware entities 714 connected to system bus 710. At least some of the hardware entities 714 perform actions involving access to and use of memory 712, which may be any type of volatile or non-volatile memory devices. Such memory can include, for example, magnetic, optical, or semiconductor based memory devices. However the various embodiments of the invention are not limited in this regard.

In some embodiments, computing system can include a user interface 702. User interface 710 can be an internal or external component of computing device 700. User interface 702 can include input devices, output devices, and software routines configured to allow a user to interact with and control software applications installed on the computing device 700. Such input and output devices include, but are not limited to, a display screen 704, a speaker (not shown), a keypad (not shown), a directional pad (not shown), a directional knob (not shown), and a microphone (not shown). As such, user interface 702 can facilitate a user-software interaction for launching software development applications and other types of applications installed on the computing device 700.

System interface 722 allows the computing device 700 to communicate directly or indirectly with the other devices, such as an external user interface or other computing devices. Additionally, computing device can include hardware entities 714, such as microprocessors, application specific integrated circuits (ASICs), and other hardware. As shown in FIG. 7, the hardware entities 714 can also include a removable memory unit 716 comprising a computer-readable storage medium 718 on which is stored one or more sets of instructions 720 (e.g., software code) configured to implement one or more of the methodologies, procedures, or functions described herein. The instructions 720 can also reside, completely or at least partially, within the memory 712 and/or within the CPU 706 during execution thereof by the computing device 700. The memory 712 and the CPU 706 also can constitute machine-readable media.

While the computer-readable storage medium 718 is shown in an exemplary embodiment to be a single storage medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure.

The term "computer-readable storage medium" shall accordingly be taken to include, but not be limited to solid-state memories (such as a memory card or other package that houses one or more read-only (non-volatile) memories, random access memories, or other re-writable (volatile) memories), magneto-optical or optical medium (such as a disk or tape). Accordingly, the disclosure is considered to include any one or more of a computer-readable storage medium or a distribution medium, as listed herein and to include recognized equivalents and successor media, in which the software implementations herein are stored.

System interface 722 can include a network interface unit configured to facilitate communications over a communications network with one or more external devices. Accordingly, a network interface unit can be provided for use with various communication protocols including the IP protocol. Network interface unit can include, but is not limited to, a transceiver, a transceiving device, and a network interface card (NIC).

While the description above refers to particular embodiments of the invention, it will be understood that many modifications may be made without departing from the spirit thereof. The accompanying claims are intended to cover such modifications as would fall within the true scope and spirit of the invention.

The exemplary embodiments have been described primarily with respect to the treatment of cancer cells and biological tissues including cancer cells, and in particular treatments that cause a change in cell function in response to applied electric fields. However, the various embodiments of the invention are not limited in this regard. Rather, the various embodiments of the invention can be used for various types of treatments, including cancer and non-cancer treatments. For example, some embodiments of the invention can be used to provide devices and methods alter the permeability of cell membranes for purposes of enhancing delivery of molecules into cancerous tissues and/or non-cancerous tissues. Such molecules can include drugs, proteins, and/or nucleic acids to name a few. In another example, some embodiments of the invention can be used for ablation therapies, such as skin ablation therapies for the removal of skin growths, wrinkles, spots, varicose veins, to name a few.

Additionally, the exemplary embodiments of the invention have been described primary with respect to non-invasive procedures. However, the various embodiments of the invention are not limited in this regard. For example, the various embodiments of the invention can also be utilized during invasive surgical procedures to treat to biological tissues exposed during such surgical procedures.

In another example, the various embodiments of the invention can be easily adapted to provide a distributor for connecting the electrodes to any number of different power supplies. Such configurations can be implemented by providing additional bias buses, contacts, and switching elements that allow a controller to select between the different power supplies.

In yet another example, the controller can simultaneous provide two or more pulsed pairs of electrodes without adverse effects to the patient. In such a configuration, the array of electrodes can be considered to comprise two or more arrays of electrodes. Thus, a pulsed pairs of electrodes can be selected for each array at the same time. According, the total exposure per unit area is effectively limited. For example, the sets of pulsed pairs can include only non-adjacent electrode pairs.

Applicants present certain theoretical aspects below that are believed to be accurate that appear to explain observations made regarding embodiments of the invention. However, embodiments of the invention may be practiced without the theoretical aspects presented. Moreover, the theoretical aspects are presented with the understanding that Applicants do not seek to be bound by the theory presented.

While various embodiments of the invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A device for treatment of biological tissues, comprising:
   a plurality of electrodes;
   at least one first electrically conductive plate defining a bias voltage bus;
   at least one second electrically conductive plate defining a reference voltage bus;
   a plurality of electrode contacts disposed between the at least one first electrically conductive plate and the at least one second electrically conductive plate, each associated with a different one of the plurality of electrodes;
   a plurality of switching elements, each comprising a pair of plungers associated with a different one of the plurality of electrode contacts, each of the pair of plungers being electrically conductive; and
   a control system for selectively controlling the plurality of switching elements to alternate between a first contact position, a second contact position, and a third contact position,
   wherein the first contact position causes a first of the pair of plungers to retract and a second of the pair of plungers to extend and electrically contact an associated one of the plurality of electrode contacts and the at least one first electrically conductive plate, wherein the second contact position causes the second of the pair of plungers to retract and the first of the pair of plungers to extend and contact the associated one of the plurality of electrode contacts and the at least one second electrically conductive plate, and wherein the third contact position causes the pair of plungers to retract so as to electrically disconnect the associated one of the plurality of electrode contacts from the at least one first electrically conductive plate and the at least one second electrically conductive plate; and
   wherein during each of a plurality of time intervals, the control system is configured for selecting the first contact position for a first contact of the plurality of electrode contacts associated with a first one of the plurality of electrodes, a second contact position for a second contact of the plurality of electrode contacts associated with a second of the plurality of electrodes adjacent to the first of the plurality of electrodes, and a third contact position for other contacts of the plurality of electrode contacts associated with the plurality of electrodes adjacent to the first and second of the plurality of electrodes,
   wherein the plurality of electrode contacts and the plurality of switching elements are disposed along concentric paths.

2. The device of claim 1, further comprising a voltage source, wherein the voltage source is configured for applying one or more voltage pulses between the bias voltage bus and the reference voltage bus.

3. The device of claim 2, wherein the one or more voltage pulses each comprise a voltage from 0.01 kV to 100 kV.

4. The device of claim 2, wherein a duration of the one or more voltage pulses is between 700 picoseconds and 2 seconds.

5. The device of claim 2, wherein a frequency of the one or more voltage pulses is between 1 Hz and 1 MHz.

6. The device of claim 2, wherein the control system is configured to alternate between the first, second, and third contact positions to cause the plurality of electrodes to provide the one or more voltage pulses.

7. The device of claim 1, wherein an electrode-to-electrode spacing for the plurality of electrodes is between 0.5 mm and 10 mm.

8. The device of claim 1, wherein each of the plurality of switching elements further comprises:
a first actuator operable to cause the first of the pair of plungers to extend and retract based on first control signals from the control system, and
a second actuator operable to cause the second of the pair of plungers to extend and retract based on second control signals from the control system.

9. The device of claim 1, wherein the plurality of switching elements are arranged along a second closed path adjacent to the first closed path.

10. The device of claim 1, wherein the first closed path is substantially circular.

11. A device for treatment of biological tissues, comprising:
a power supply for generating electrical pulses:
an array of electrodes;
a distributor comprising a first electrically conductive plate coupled to a high voltage terminal of the power supply, a second electrically conductive plate coupled to a reference voltage terminal of the power supply, a plurality of electrode contacts disposed between the first and second electrically conductive plates and electrically isolated from the first and second electrically conductive plates, each of the plurality of electrode contacts electrically coupled to a different one of the electrodes, and a plurality of switching elements, each comprising a pair of plungers associated with a different one of the plurality of electrode contacts, each of the pair of plungers being electrically conductive; and
a controller for selectively controlling the plurality of switching elements to alternate between a first contact position, a second contact position, and a third contact position,
wherein the first contact position causes a first of the pair of plungers to retract and a second of the pair of plungers to extend and electrically contact an associated one of the plurality of electrode contacts and the at least one first electrically conductive plate, wherein the second contact position causes the second of the pair of plungers to retract and the first of the pair of plungers to extend and contact the associated one of the plurality of electrode contacts and the at least one second electrically conductive plate, and wherein the third contact position causes the pair of plungers to retract so as to electrically disconnect the associated one of the plurality of electrode contacts from the at least one first electrically conductive plate and the at least one second electrically conductive plate,
wherein the plurality of electrode contacts and the plurality of switching elements are disposed along concentric paths, and
wherein during each of a plurality of time intervals, the controller is configured for selecting the first contact position for a first one of the plurality of electrode contacts associated with a first one of the electrodes, a second contact position for a second one of the plurality of electrode contacts associated with a second of the electrodes adjacent to the first of the electrodes, and a third contact position for other ones of the plurality of electrode contacts associated with other ones of the electrodes adjacent to the first and second of the electrodes.

12. The device of claim 11, further comprising a substrate portion mechanically coupled to an endpiece portion of the distributor, the substrate portion configured for supporting the array of electrodes.

13. The device of claim 12, wherein the substrate is removably coupled to the endpiece portion.

14. The device of claim 11, wherein the power supply is configured for generating voltage pulses comprising a voltage from 0.01 kV to 100 kV, a duration from 700 picoseconds to 2 seconds, and a frequency between 1 Hz and 1 MHz.

15. The device of claim 11, wherein the plurality of switching elements associated with each one of the electrodes each comprise:
a first actuator for causing the first of the pair of plungers to extend and retract based on first control signals from the controller, and
a second actuator for causing the first of the pair of plungers to extend and retract based on second control signals from the controller.

16. The device of claim 15, wherein the first and second actuators comprise linear actuators.

17. The device of claim 11, wherein an electrode-to-electrode spacing for the array of electrodes is between 0.5 mm and 10 mm.

18. The device of claim 11, wherein the array of electrodes comprise a plurality of penetrating needles.

19. The device of claim 11, wherein the array of electrodes comprise a plurality of nonpenetrating pins.

20. A method for treating or manipulating biological tissues, comprising:
placing a biological tissue in contact with an array of electrodes;
applying one or more electrical pulses to the array of electrodes via a distributor comprising a first electrically conductive plate coupled to a high voltage terminal of a power supply, a second electrically conductive plate coupled to a reference voltage terminal of the power supply, a plurality of electrode contacts disposed between the first and second electrically conductive plates and electrically isolated from the first and second electrically conductive plates, each of the plurality of electrode contacts electrically coupled to a different one of the electrodes, and a plurality of switching elements, each comprising a pair of plungers associated with a different one of the plurality of electrode contacts, each of the pair of plungers being electrically conductive, and wherein the plurality of electrode contacts and the plurality of switching elements are disposed along concentric paths; and
operating the plurality of switching elements over a plurality of time intervals,
wherein during each of the plurality of time intervals, a control system is configured for selecting a first contact position for a first one of the plurality of electrode contacts associated with a first electrode of the array of electrodes, a second contact position for a second one of the plurality of electrode contacts associated with a second electrode of the array of electrodes adjacent to the first electrode of the array of electrodes, and a third contact position for ones of the plurality of electrode contacts associated with other electrodes of the array of electrodes adjacent to the first and second electrodes of the array of electrodes.

21. The method of claim 20, wherein the step of applying further comprises selecting the one or more electrical pulses to provide voltage difference from 0.01 kV to 100 kV.

22. The method of claim 20, wherein the step of applying further comprises selecting the one or more electrical pulses to have a duration between 700 picoseconds and 2 seconds.

23. The method of claim 20, wherein the step of applying further comprises selecting the one or more electrical pulses to have a frequency of the voltage pulses is between 1 Hz and 1 MHz.

24. The method of claim 20, wherein the step of placing further comprises selecting the array of electrodes to comprise at least a 2×2 array of electrodes, and wherein the step of operating further comprises:

selecting as the first one electrode and the second one electrode of the array of electrodes a first diagonal pair of electrodes of the 2×2 array of electrodes during a first of the plurality time intervals, and selecting as the first one and the second one electrode of the array of electrodes a second diagonal pair of electrodes of the 2×2 array of electrodes during a second of the plurality time intervals.

25. The method of claim 20, wherein the step of operating further comprises:

determining a location of the biological tissue relative to positions of electrodes in the array of electrodes, identifying a portion of the electrodes in the array of electrodes capable of producing an electric field capable of inducing a cell effect in the biological tissue, and selecting the first electrode and the second electrode of the array of electrodes from the identified portion of the electrodes.

* * * * *